United States Patent
Takahashi et al.

(10) Patent No.: US 7,264,790 B2
(45) Date of Patent: Sep. 4, 2007

(54) 1,3-GLYCERIDE COMPOUND HAVING TWO IODOPHENYL GROUPS

(75) Inventors: Kazunobu Takahashi, Minami-ashigara (JP); Hiroshi Kitaguchi, Minami-ashigara (JP); Kazuhiro Aikawa, Minami-ashigara (JP)

(73) Assignee: Fujifilm Corporation, Tokyo (JP)

( * ) Notice: Subject to any disclaimer, the term of this patent is extended or adjusted under 35 U.S.C. 154(b) by 309 days.

(21) Appl. No.: 10/487,319

(22) PCT Filed: Aug. 22, 2002

(86) PCT No.: PCT/JP02/08461

§ 371 (c)(1),
(2), (4) Date: Aug. 20, 2004

(87) PCT Pub. No.: WO03/018530

PCT Pub. Date: Mar. 6, 2003

(65) Prior Publication Data

US 2005/0002864 A1   Jan. 6, 2005

(30) Foreign Application Priority Data

Aug. 23, 2001 (JP) .............. 2001-253395
Jun. 24, 2002 (JP) .............. 2002-182351

(51) Int. Cl.
*A61K 49/00* (2006.01)
*C07C 53/00* (2006.01)
*C07C 57/00* (2006.01)
*C07C 59/00* (2006.01)
*C08G 63/48* (2006.01)
*A61K 49/04* (2006.01)

(52) U.S. Cl. .............. 424/1.21; 554/1; 424/9.1

(58) Field of Classification Search .......... 424/1.21, 424/9.4; 554/1
See application file for complete search history.

(56) References Cited

U.S. PATENT DOCUMENTS 4,873,075 A * 10/1989 Counsell et al. .......... 424/1.85
2003/0180220 A1 * 9/2003 Aikawa et al. .......... 424/9.4

FOREIGN PATENT DOCUMENTS

WO   WO 01/93918 A2   12/2001

OTHER PUBLICATIONS

Hartman, L Advances in the synthesis of glycerides of fatty acids Chem. Rev. 1958, 13, 845.*

* cited by examiner

*Primary Examiner*—Michael G. Hartley
*Assistant Examiner*—Melissa Perreira
(74) *Attorney, Agent, or Firm*—Sughrue Mion, PLLC (57) ABSTRACT

A compound represented by the following general formula (I) or a salt thereof:

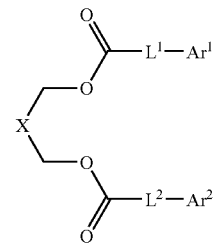

wherein $Ar^1$ and $Ar^2$ independently represent a substituted or unsubstituted aryl group having at least one iodine atom as a substituent; $L^1$ and $L^2$ independently represent a divalent bridging group of which main chain consists of 7 or more atoms at least one of which is a heteroatom; and X represents —CH(OH)— or —CO—, which is suitable for an iodine-containing contrast medium containing liposomes.

17 Claims, 2 Drawing Sheets

1,3-GLYCERIDE COMPOUND HAVING TWO IODOPHENYL GROUPS

TECHNICAL FIELD

The present invention relates to a 1,3-diacylglyceride compound having two iodophenyl groups. The present invention also relates to a liposome which contains the compound as a membrane component and a contrast medium for X-ray radiography which contains said liposome.

BACKGROUND ART

In the field of X-ray angiography utilizing an iodine compound, a technique is available which comprises administration of a water-soluble iodine-containing contrast medium for visualization of vascular flows, and detection of lesions at which the flows are obstructed. However, in the aforementioned method, the iodine-containing contrast medium is present in the vascular flows to detect changes of vascular flows inside the vessels, and the method has difficulty in distinguishing the lesions from normal tissues as compared to a method wherein an iodine-containing contrast medium is localized in cells consisting a lesion. For this reason, by the above method, only a lesion where constriction progresses 50% or more can be detected, and it is difficult to detect a lesion before the onset of attack of an ischemic disease.

Separately, attempts have also been reported in which a hydrophobic iodine-containing contrast medium or a hydrophilic contrast medium is formulated for selective accumulation in a target lesion (International Publications WO95/19186, WO95/21631, WO89/00812, British Patent No. 867650, WO96/00089, WO94/19025, WO96/40615, WO95/2295, WO98/41239, WO98/23297, WO99/02193, WO97/06132, U.S. Pat. Nos. 4,192,859, 4,567,034, 4,925,649, Pharm. Res., 6 (12), 1011 (1989); Pharm. Res., 16 (3), 420 (1999); J. Pharm. Sci., 72 (8), 898 (1983); Invest. Radiol., 18 (3), 275 (1983)). For example, Pharm. Res., 6 (12), 1011 (1989) discloses that injection of an oil-particle dispersion of cholesterol iopanoate as a hydrophobic compound allows accumulation of the iodine compound in arteriosclerotic lesions of experimental animals. Further, Pharm. Res., 16 (3), 420 (1999) discloses that administration of cholesterol iopanoate after being taken up into acetyl-LDL allows accumulation of the iodine compound in arteriosclerotic lesions of experimental animals.

Further, J. Pharm. Sci. 72 (8), 898 (1983) discloses examples of X-ray hepatography and splenography by injection of an oil-particle dispersion of cholesterol iopanoate. U.S. Pat. No. 4,567,034 describes a method of selective hepatography or splenography utilizing liposomes encapsulating an ester of diatrizoic acid. International Publications WO96/28414 and WO96/00089 disclose contrast media for imaging vascular pools or lymphatic systems. However, the methods using these formulations are not satisfactory in efficiency and selectivity for a purpose of selective contrast of vascular diseases, and no example thereof is reported in which vascular diseases are imaged by utilizing X-ray irradiation.

Further, methods have been reported in which a triglyceride compound comprising an alkylcarboxylic acid having two 3-amino-2,4,6-triiodophenyl groups and a saturated/unsaturated fatty acid is formulated as an oil particle dispersion (lipid emulsion) or a Tween 20 dispersion and used for the purpose of hepatography or imaging of blood-pool (Radiology, 216 (3) 865 (2000); Invest. Radiol., 35 (3), 158 (2000); International Publication WO98/46275; J. Pharm. Sci., 85 (9), 908 (1996); Pharm. Res., 13 (6), 875 (1996); International Publication WO95/31181; J. Med. Chem., 38 (4), 636 (1995); Invest. Radiol., 29 (SUPPL. 2), S284 (1994); International Publication WO94/19025; U.S. Pat. No. 4,873,075; Appl. Radiol. Isot., 37 (8), 907 (1986); J. Med. Chem., 29 (12), 2457 (1986)).

International Publication WO01/93918 discloses an example of radiological imaging of arteriosclerotic lesions in which a hydrophobic and hydrolysis-resistant radioactive iodine-containing contrast medium is formulated as a microemulsion or taken up into acetyl-LDL and then administered to experimental animals. Furthermore, it has been reported that the aforementioned cholesterol iopanoate is not metabolized in living bodies and accumulated in living organs, especially in liver (J. Med. Chem., 25, 1500 (1982)). The above property of the compound means that the compound remains in living bodies over a prolonged period of time, which is considered as an undesired property when a diagnostic purpose such as a contrast medium for X-ray radiography is intended.

From an aspect of compounds, U.S. Pat. No. 4,873,075 and J. Med. Chem., 29 (12), 2457 (1986) mentioned above contain descriptions of diacyl-1,3-glyceride compounds comprising an alkylcarboxylic acid containing two 3-amino-2,4,6-triiodophenyl groups and oxidized compounds thereof. However, no purpose thereof other than as synthetic intermediates is described.

DISCLOSURE OF THE INVENTION

An object of the present invention is to provide an iodine compound suitable for iodine contrast media containing liposomes for selectively imaging lesions. The inventors of the present invention conducted studies to achieve the foregoing object, and as a result, they found that 1,3-diacylglycerin derivatives having two iodophenyl groups and 2-oxidized compounds thereof had superior properties as components for constituting liposomes, as being a contrast medium for X-ray radiography, and lesions of vascular diseases were successfully imaged selectively by X-ray radiography utilizing the liposomes containing said compounds. They also found that the compounds had a property that they were metabolized in the liver after the radiography and did not accumulate in vivo. The present invention was achieved on the basis of these findings.

The present invention thus provides a compound represented by the following general formula (I) or a salt thereof:

(I)

[in the formula, $Ar^1$ and $Ar^2$ independently represent a substituted or unsubstituted aryl group having at least one iodine atom as a substituent; $L^1$ and $L^2$ independently represent a divalent bridging group of which main chain consists of 7 or more atoms and at least one of the atoms consisting of said main chain is a heteroatom; and X represents —CH(OH)— or —CO—]. As preferred embodiments of the present invention, provided are the aforementioned compound or a salt thereof, wherein X is —CH(OH)—; and the aforementioned compound or a salt thereof, wherein $Ar^1$ and $Ar^2$ independently represent a phenyl group having at least three iodine atoms as substituents.

From another aspect, the present invention provides a liposome containing the compound represented by the aforementioned general formula (I) or a salt thereof as a membrane component. As preferred embodiments of the present invention, provided is the aforementioned liposome, which contains a combination of a phosphatidylcholine and a phosphatidylserine as membrane components. The present invention also provides use of the compound represented by the aforementioned general formula (I) for the manufacture of the aforementioned liposome.

The present invention also provides a contrast medium for X-ray radiography, which comprises the aforementioned liposome. As preferred embodiments of the invention, provided are the aforementioned contrast medium for X-ray radiography, which is used for radiography of a vascular disease; the aforementioned contrast medium for X-ray radiography, which is used for radiography of vascular smooth muscle cells which are abnormally proliferated under an influence of foam macrophages; the aforementioned contrast medium for X-ray radiography, which is used for radiography of a tissue or a lesion in which macrophages localizes; the aforementioned contrast medium for X-ray radiography, wherein the tissue in which macrophages localize is selected from the group consisting of tissues of liver, spleen, air vesicle, lymph node, lymph vessel, and renal epithelium; and the aforementioned contrast medium for X-ray radiography, wherein the lesion in which macrophages localize is selected from the group consisting of lesions of tumor, inflammation, and infection.

The present invention also provides use of the aforementioned compound or a salt thereof for the manufacture of the aforementioned contrast medium for X-ray radiography; a method for X-ray radiography, which comprises the steps of administering liposomes containing the aforementioned compound as a membrane component to a mammal including human and then irradiating the mammal with an X-ray; and a method for imaging a lesion of a vascular disease, which comprises the steps of administering liposomes containing the aforementioned compound as a membrane component to a mammal including human and then irradiating the mammal with an X-ray.

The present invention further provides a liposome, which contains, as a membrane component, the aforementioned compound or a salt thereof at least one of which iodine atoms is a radioisotope, and a contrast medium for scintigraphy, which comprises the aforementioned liposome. As preferred embodiments of the invention, provided are the aforementioned contrast medium for scintigraphy, which is used for scintigraphy of vascular smooth muscle cells which are abnormally proliferated under an influence of foam macrophages; the aforementioned contrast medium for scintigraphy, which is used for scintigraphy of a tissue or lesion where macrophages localize; the aforementioned contrast medium for scintigraphy, wherein the tissue as the object of scintigraphy is selected from the group consisting of blood vessel, liver, spleen, air vesicle, lymph node, lymph vessel, and renal epithelium; and the aforementioned contrast medium for scintigraphy, which is used for scintigraphy of a lesion selected from the group consisting of lesions of tumor, arteriosclerosis, inflammation, and infection.

The present invention also provides use of the aforementioned compound or a salt thereof for manufacture of the aforementioned contrast medium for scintigraphy; a method for scintigraphy, which comprises the steps of administering liposomes containing the aforementioned compound as a membrane component to a mammal including human and then detecting radioactivity emitted by the liposomes; and a method for scintigraphy of a lesion of vascular disease, which comprises the steps of administering liposomes containing the aforementioned compound as a membrane component to a mammal including human and then detecting radioactivity emitted by the liposomes.

BEST MODE FOR CARRYING OUT THE INVENTION

When a functional group is referred to as "substituted or unsubstituted" or "may be substituted" in the specification, the functional group is meant to have one or more substituents. Unless otherwise specifically mentioned, number, substituting position, and type of a substituent to be bound are not particularly limited. When a functional group has two or more substituents, they may be the same or different. In the specification, when a functional group has a substituent, example of the substituent include a halogen atom (the "halogen atom" herein referred to may be any of fluorine, chlorine, bromine, and iodine), an alkyl group (the "alkyl group" herein referred to may be any of straight, branched, cyclic, and a combination thereof, and the cyclic alkyl group include a polycyclic alkyl group such as a bicycloalkyl group. Alkyl moieties of other substituents containing the alkyl moieties have the same meaning), an alkenyl group (including a cycloalkenyl group and a bicycloalkenyl group), an alkynyl group, an aryl group, a heterocyclic group, cyano group, hydroxyl group, nitro group, carboxyl group, an alkoxyl group, an aryloxy group, a silyloxy group, a heterocyclyloxy group, an acyloxy group, a carbamoyloxy group, an alkoxycarbonyloxy group, an aryloxycarbonyloxy group, an amino group (including an anilino group), an acylamino group, an aminocarbonylamino group, an alkoxycarbonylamino group, an aryloxycarbonylamino group, a sulfamoylamino group, an alkyl or arylsulfonylamino group, a mercapto group, an alkylthio group, an arylthio group, a heterocyclylthio group, a sulfamoyl group, sulfo group, an alkyl or arylsulfinyl group, an alkyl or arylsulfonyl group, an acyl group, an aryloxycarbonyl group, an alkoxycarbonyl group, a carbamoyl group, an aryl or heterocyclylazo group, an imido group, a phosphino group, a phosphinyl group, a phosphinyloxy group, a phosphinylamino group, and a silyl group.

In the aryl group substituted with at least one iodine atom, which is represented by $Ar^1$ or $Ar^2$, number of iodine atoms on the aryl ring is preferably 2 or more, most preferably 3 or more. The maximum number of iodine atoms is not particularly limited. The number of iodine atoms is usually 5 or less. The type of the aryl group represented by $Ar^1$ or $Ar^2$ is not particularly limited. Anthracene group, naphthalene group, phenyl group and the like are preferred, and phenyl group is most preferred. When $Ar^1$ or $Ar^2$ represent mono- or diiodophenyl group, the substituting positions of the iodine atoms on the benzene ring are not particularly limited. When $Ar^1$ or $Ar^2$ represent a triiodophenyl group, the substituting positions of the three iodine atoms on the benzene ring are not particularly limited. For example, substitutions at "2,4,and 6-positions", "2,3,and 5-positions", and "3,4,and 5-positions" are preferred, substitutions at "2,4,and 6-positions", and "2,3,and 5-positions" are more preferred, and substitutions at "2,4,and 6-positions" are most preferred.

The aryl group represented by $Ar^1$ or $Ar^2$ may be substituted on the ring. The type, number, and substituting position of the substituent on the ring are not particularly limited. When the aryl ring is substituted, preferred examples of the substituents include a halogen atom, an alkyl group, cyano group, hydroxyl group, an alkoxyl group, amino group, an acylamino group, an acyl group, carboxyl group, an alkoxycarbonyl group, and a carbamoyl group. Further, it is also preferred that the aryl group represented by $Ar^1$ or $Ar^2$ does not have any substituent other than the iodine atom(s).

$L^1$ and $L^2$ represent a divalent bridging group of which main chain has at least one heteroatom (the "heteroatom" referred to in this specification means an arbitrary atom other than carbon atom, such as nitrogen atom, oxygen atom, and sulfur atom), wherein said main chain is constituted by 7 or more atoms. In the specification, the "main chain" means an atomic group which connects —O—CO— and the group represented by Ar with a minimum number of atoms. The bridging group may be a saturated group, or may contain an unsaturated bond. Although the number of the heteroatom in the main chain is not particularly defined, the number is preferably 5 or less, more preferably 3 or less pieces, most preferably 1. The position of the heteroatom in the main chain is not particularly limited. When the number of the heteroatom is 1, the position is preferably within 5 atoms from the Ar group. The bridging group may contain a functional group as a partial structure which contains a carbon atom subsequent to the heteroatom. Examples of the unsaturated moiety and/or the functional group containing a heteroatom in the bridging group include, for example, an alkenyl group, an alkynyl group, an ester group (including carboxylic acid ester, carbonic acid ester, sulfonic acid ester and sulfonic acid ester), an amido group (including carbonamido, urethane, sulfonamido and sulfinamido), an ether group, a thioether group, a disulfide group, an amino group, an imido group. The aforementioned functional group may further be substituted, and each of $L^1$ and $L^2$ may independently have plural substituents. When two or more substituents exist, they may be the same or different.

The partial structure of the divalent bridging group represented by $L^1$ or $L^2$ is preferably an alkenyl group, an ester group, an amido group, an ether group, a thioether group, a disulfide group, or an amino group, more preferably an alkenyl group, an ester group, or an ether group. The heteroatom contained in the main chain is preferably oxygen atom or sulfur atom, and oxygen atom is most preferred. The carbon number of $L^1$ and $L^2$ is preferably 7 to 30, more preferably 10 to 25, most preferably 10 to 20. $L^1$ and $L^2$ may be substituted. When they are substituted, the substituent may preferably be a halogen atom or an alkyl group. Further, they are also preferably unsubstituted groups.

Preferred embodiments of $L^1$ and $L^2$ are specifically exemplified below. However, the bridging group in the compound of the present invention is not limited to these examples. In the following examples, the groups bind to Ar at the right ends. —$(CH_2)_n$—O—, —$(CH_2)_m$—S—$CH_2$—, —$(CH_2)_m$—(C=O)O—, —$(CH_2)_m$—(C=O)NH—, —$(CH_2)_m$—O(C=O)—, —$(CH_2)_m$—NH(C=O)—, —$(CH_2)_s$—NH(C=O)—$(CH_2)_2$—O—, —$CH_2$—CH=CH—$(CH_2)_t$—O—, and —$(CH_2)_m$—CH(CH_3)—O— (n represents an arbitrary integer of 10 to 20; m represents an arbitrary integer of 9 to 19; s represents an arbitrary integer of 8 to 18; and t represents an arbitrary integer of 7 to 17). In the aforementioned general formula (I), X represents —CH(OH)— or —CO—, and X is preferably —CH(OH)—.

Among the compounds of the present invention, those wherein X represents —C(OH)— have one asymmetric carbon, and the compounds of the present invention may further have one or more asymmetric carbons depending on the types of substituents. Therefore, stereoisomers such as optically active substances and diastereomers based on the asymmetric carbons may exist. Any of optically active substances based on the asymmetric carbons, racemates, arbitrary stereoisomers in pure forms, arbitrary mixtures of stereoisomers, racemates and so forth fall within the scope of the present invention. Further, the compounds of the present invention may have an olefinic double bond. The configuration may be either E-configuration or Z-configuration, or the compounds may be present as a mixture thereof. The compounds of the present invention may also exist as tautomers. Any tautomers or mixtures thereof fall within the scope of the present invention. Further, the compound of the present invention may form a salt depending on the type of a substituent, and the compound in a free form or the compound in a form of a salt may form a hydrate or a solvate. All of these substances also fall within the scope of the present invention.

Preferred examples of the compounds of the present invention are shown below. However, the compounds of the present invention are not limited to these examples.

(1-1)

1: n = m = 6        11: n = m = 18
2: n = m = 8        12: n = m = 20
3: n = m = 10      13: n = m = 25
4: n = m = 11      14: n = m = 30
5: n = m = 12      15: n = 10,
6: n = m = 13              m = 14
7: n = m = 14
8: n = m = 15
9: n = m = 16
10: n = m = 17

-continued (1-2)

1: n = 6
2: n = 10
3: n = 12
4: n = 14
5: n = 16
6: n = 18
7: n = 20

(1-3)

1: n = 5
2: n = 9
3: n = 11
4: n = 13
5: n = 15
6: n = 17
7: n = 19

(1-4)

1: n = 5
2: n = 9
3: n = 11
4: n = 13
5: n = 14
6: n = 15
7: n = 17
8: n = 19

-continued (1-5)

1: n = 5
2: n = 9
3: n = 11
4: n = 13
5: n = 15
6: n = 17
7: n = 19

(1-6)

1: n = 5
2: n = 9
3: n = 11
4: n = 13
5: n = 15
6: n = 17
7: n = 19

(1-7)

1: n = 5
2: n = 9
3: n = 11
4: n = 13
5: n = 15
6: n = 17
7: n = 19

(1-8)

1: n = 2
2: n = 6
3: n = 8
4: n = 10
5: n = 12
6: n = 14
7: n = 16

(1-9)

1: n = 3
2: n = 7
3: n = 9
4: n = 11
5: n = 13
6: n = 16
7: n = 17

(1-10)

(1-11)

(1-12)

1: n = m = 6      11: n = m = 18
2: n = m = 8      12: n = m = 20
3: n = m = 10    13: n = m = 25
4: n = m = 11    14: n = m = 30
5: n = m = 12    15: n = 10,
6: n = m = 13           m = 14
7: n = m = 14
8: n = m = 15
9: n = m = 16
10: n = m = 17

(1-13)

1: n = m = 6      11: n = m = 18
2: n = m = 8      12: n = m = 20
3: n = m = 10    13: n = m = 25
4: n = m = 11    14: n = m = 30
5: n = m = 12    15: n = 10,
6: n = m = 13           m = 14
7: n = m = 14
8: n = m = 15
9: n = m = 16
10: n = m = 17

-continued (2-1)

1: n = m = 6    11: n = m = 18
2: n = m = 8    12: n = m = 20
3: n = m = 10   13: n = m = 25
4: n = m = 11   14: n = m = 30
5: n = m = 12   15: n = 10, m = 14
6: n = m = 13
7: n = m = 14
8: n = m = 15
9: n = m = 16
10: n = m = 17

(2-2)

1: n = 6
2: n = 10
3: n = 12
4: n = 14
5: n = 16
6: n = 18
7: n = 20

(2-3)

1: n = 5
2: n = 9
3: n = 11
4: n = 13
5: n = 15
6: n = 17
7: n = 19

(2-4)

1: n = 5
2: n = 9
3: n = 11
4: n = 13
5: n = 14
6: n = 15
7: n = 17
8: n = 19

(2-5)

1: n = 5
2: n = 9
3: n = 11
4: n = 13
5: n = 15
6: n = 17
7: n = 19

(2-6)

1: n = 5
2: n = 9
3: n = 11
4: n = 13
5: n = 15
6: n = 17
7: n = 19

-continued (2-7)

1: n = 5
2: n = 9
3: n = 11
4: n = 13
5: n = 15
6: n = 17
7: n = 19

(2-8)

1: n = 2
2: n = 6
3: n = 8
4: n = 10
5: n = 12
6: n = 14
7: n = 16

(2-9)

1: n = 3
2: n = 7
3: n = 9
4: n = 11
5: n = 13
6: n = 16
7: n = 17

-continued

(2-10)

(2-11)

(2-12)

1: n = m = 6      11: n = m = 18
2: n = m = 8      12: n = m = 20
3: n = m = 10    13: n = m = 25
4: n = m = 11    14: n = m = 30
5: n = m = 12    15: n = 10,
6: n = m = 13            m = 14
7: n = m = 14
8: n = m = 15
9: n = m = 16
10: n = m = 17

-continued (2-13)

| | |
|---|---|
| 1: n = m = 6 | 11: n = m = 18 |
| 2: n = m = 8 | 12: n = m = 20 |
| 3: n = m = 10 | 13: n = m = 25 |
| 4: n = m = 11 | 14: n = m = 30 |
| 5: n = m = 12 | 15: n = 10, |
| 6: n = m = 13 | m = 14 |
| 7: n = m = 14 | |
| 8: n = m = 15 | |
| 9: n = m = 16 | |
| 10: n = m = 17 | |

Synthetic methods for the compounds of the present invention represented by the general formula (I), in general, will be explained below. However, synthetic methods of the compounds of the present invention are not limited to these methods. As starting materials for preparation which have an iodoaryl group, especially triiodophenyl group, as being a partial structure of the compounds of the present invention, those ordinarily commercially available may be used, or they may be suitably synthesized depending on purposes. As commercially available products, for example, 2,4,6-triiodophenol and benzoic acid derivatives (for example, 3-amino-2,4,6-triiodobenzoicacid, acetrizoic acid, iopipamide, diatrizoic acid, histodenz, 5-amino-2,4,6-triiodoisophthalic acid, 2,3,5-triiodobenzoic acid, tetraiodo-2-sulfobenzoic acid), iopanoic acid, iophenoxic acid and the like can be used. When the compounds are obtained by syntheses, iodine atoms can be introduced on an aromatic ring by, for example, the method described by Richard C. Larock in Comprehensive Organic Transformations (VCH) for use as raw materials.

The aforementioned triiodophenyl derivatives sometimes have a functional group such as hydroxyl group, amino group, thiol group, and carboxyl group as a partial structure. These functional groups can also be condensed with a dibasic carboxylic acid, halogenated aliphatic acid, hydroxy aliphatic acid or the like via an ether bond, ester bond, amino bond, amide bond or the like to prepare a carboxylic acid having a triiodophenyl group, and the resulting compound can be used as synthetic intermediates for the compounds of the present invention. In these steps, a protective group may also be used, if necessary. As the protective group, for example, those described by T. W. Green & P. G. M. Wuts in Protecting Groups in Organic Synthesis (John Wiley & Sons, Inc.) can be appropriately chosen and used. Examples of the dibasic carboxylic acid include, for example, dodecanedioic acid, tetradecanedioic acid, docosanedioic acid, 4,4'-dithiobutanedioic acid and the like. Examples of the halogenated aliphatic acid include, for example, 12-bromododecanoic acid and 16-bromohexadecanoic acid. Examples of the hydroxy aliphatic acid include, for example, 10-hydroxydecanoic acid, 12-hydroxydodecanoic acid, 12-hydroxystearic acid and the like. However, the dibasic carboxylic acids are not limited to these examples.

The compounds of the present invention may have an alkyl group with any length as the divalent bridging group represented by $L^1$ and $L^2$, and if no suitable synthetic raw material is available, a raw material can be appropriately obtained by synthesis using a suitable starting material. Examples of the synthetic methods include, for example, Wittig reaction, Barbier-Wieland degradation, Arndt-Eistert synthesis, a method using acetylide (according to, for example, the method described in Tetrahedron Lett., 35, 9501 (1994)), a method using a chloroformic acid ester (described in, for example, Synthesis, 427 (1986)), a method using diethyl malonate (described in, for example, Arch. Pharm. (Weinheim) 328, 271 (1995)) and the like. However, the above methods are given as examples, and the synthetic methods are not limited to these examples.

Carboxylic acids having triiodophenyl group can be derived into the compounds of the present invention by, for example, the method described in J. Med. Chem., 29 (12), 2457 (1986). The compounds of the present invention can also be synthesized by, for example, performing esterification, deprotection/reduction, and esterification stepwise from a glycerin derivative such as glyceraldehyde, and 2,2-dimethyl-1,3-dioxolane-4-methanol.

The compounds of the present invention can be used as membrane components of liposomes, and such liposomes can be used as active ingredients of X-ray contrast media. In the liposome containing the compound of the present invention, a content of the compound of the present invention is about from 10 to 90 mass %, preferably from 10 to 80 mass %, further preferably from 20 to 80 mass %, based on the total membrane components of the liposome. One kind of the compound of the present invention may be used as a membrane component, or two or more kinds of the compounds of the present invention may be used in combination.

As other components constituting the liposome membrane, any of lipid compounds ordinarily used for preparation of liposomes can be used. For example, such compounds are described in Biochim. Biophys. Acta, 150 (4), 44 (1982); Adv. in Lipid. Res., 16 (1) 1 (1978); "RESEARCH IN LIPOSOMES", P. Machy, L. Leserman, John Libbey EUROTEXT Co.; "Liposome" (Ed., Nojima, Sunamoto and Inoue, Nankodo) and the like. As the lipid compounds, phospholipids are preferred, and phosphatidylcholines (PC) are particularly preferred. Preferred examples of phosphatidylcholines include, but not limited thereto, egg PC, dimyristoyl-PC (DMPC), dipalmitoyl-PC (DPPC), distearoyl-PC (DSPC), dioleyl-PC (DOPC) and the like.

According to a preferred embodiment of the liposome of the present invention, a phospholipid selected from the group consisting of phosphatidylcholines and phosphatidylserines (PS) can be used as a membrane component of the liposome, and according to a more preferred embodiment, the both can be used in combination. Examples of the phosphatidylserines include those having lipid moieties similar to those of the phospholipids mentioned as preferred examples of the phosphatidylcholines. When a phosphatidylcholine and a phosphatidylserine are used in combination, molar ratio of PC and PS (PC:PS) used is preferably in the range of 90:10 to 10:90, further preferably in the range of 30:70 to 70:30.

Another preferred embodiment of the liposome of the present invention includes the liposome containing phosphatidylcholine and phosphatidylserine and further containing a phosphoric acid dialkyl ester as membrane components. The two alkyl groups constituting the dialkyl ester of phosphoric acid are preferably the same kind, and each alkyl group may contain 6 or more carbon atoms, preferably 10 or more carbon atoms, more preferably 12 or more carbon atoms. An upper limit of the carbon numbers of the alkyl groups is not particularly limited. The limit is generally 24 or less. Preferred examples of the phosphoric acid dialkyl ester include, but not limited thereto, dilauryl phosphate, dimyristyl phosphate, dicetyl phosphate and the like. In this embodiment, preferred amount of the phosphoric acid dialkyl ester is from 1 to 50 mass %, preferably from 1 to 30 mass %, further preferably from 1 to 20 mass %, based on the total mass of phosphatidylcholine and phosphatidylserine.

In the liposome containing a phosphatidylcholine, a phosphatidylserine, a phosphoric acid dialkyl ester and the compound of the present invention as membrane components, preferred weight ratios of PC, PS, phosphoric acid dialkyl ester and the compound of the present invention may be chosen from 5 to 40 mass %: from 5 to 40 mass %: from 1 to 10 mass %: from 15 to 80 mass %.

The components of the liposome of the present invention are not limited to the aforementioned four kinds of compounds, and other components may be admixed. Examples of such components include cholesterol, cholesterol esters, sphingomyelin, monosial ganglioside GM1 derivatives described in FEBS Lett., 223, 42 (1987); Proc. Natl. Acad. Sci., USA, 85, 6949 (1988) etc., glucuronic acid derivatives described in Chem. Lett., 2145 (1989); Biochim. Biophys. Acta, 1148, 77 (1992) etc., polyethylene glycol derivatives described in Biochim. Biophys. Acta, 1029, 91 (1990); FEBS Lett., 268, 235 (1990) and the like. However, the components are not limited to these examples.

The liposome of the present invention can be prepared by any methods known in the field of the art. Examples of the preparation method are described in the references as general review of liposomes mentioned above, as well as in Ann. Rev. Biophys. Bioeng., 9, 467 (1980), "Liopsomes" (Ed. by M. J. Ostro, MARCELL DEKKER, INC.) and the like. Specific examples thereof include the ultrasonication method, ethanol injection method, French press method, ether injection method, cholic acid method, calcium fusion method, freeze and thawing method, reverse phase evaporation method and the like. However, the preparation methods are not limited to these examples. Size of the liposomes may be any of those obtainable by the aforementioned methods. Generally, a size in average may be 400 nm or less, preferably 200 nm or less. Structures of the liposomes are not particularly limited, and may be unilamellar or multilamellar structure. It is also possible to formulate one or more kinds of appropriate medicaments or other contrast media in the liposomes.

The liposomes of the present invention can be used as a contrast medium, preferably contrast medium for X-ray radiography. The contrast medium of the present invention can be preferably administered parenterally, more preferably administered intravenously. For example, preparations in the form of an injection or a drip infusion can be provided as powdery compositions in a lyophilized form, and they can be used by being dissolved or resuspended just before use in water or an appropriate solvent (e.g., physiological saline, glucose infusion, buffering solution and the like). When the liposomes of the present invention are used as a contrast medium for X-ray radiography, the dose can be suitably determined so that an iodine content in the liposomes becomes similar to that of a conventional contrast medium for X-ray radiography.

Although it is not intended to be bound by any specific theory, it is known that, in vascular diseases such as arteriosclerosis or restenosis after PTCA, vascular smooth muscle cells are abnormally proliferated and migrate into endosporium at the same time to narrow blood flow passages. Factors triggering the abnormal proliferation of normal vascular smooth muscle cells have not yet been clearly elucidated, however, it is known that migration of macrophages into endosporium and foaming are important factors. It is reported that vascular smooth muscle cells then cause phenotype conversion (from constricted to composite type).

When the liposomes of the present invention are used, the iodine compounds of the present invention can be selectively taken up into the vascular smooth muscle cells abnormally proliferated under influences of foam macrophages. By using the liposomes of the present invention, iodine compounds can be accumulated in smooth muscle cells in a larger amount compared with a contrast medium utilizing a suspension or an oil emulsion as a known technique. As a result, by using the liposomes of the present invention, X-ray radiography with high contrast between a lesion and vascular smooth muscle cells in non-pathological sites is achievable. Therefore, the contrast medium of the present invention can be suitably used particularly for radiography of vascular diseases. For example, radiography of arteriosclerotic lesion or restenosis after PTCA can be performed.

Further, as described in J. Biol. Chem., 265, 5226 (1990), for example, it is known that liposomes containing phospholipids, particularly liposomes formed by using PC and PS, likely to accumulate on macrophages with the aid of scavenger receptors. Therefore, by using the liposomes of the present invention, the iodine compound of the present invention can be accumulated in a tissue or a lesion in which macrophages localize. When the liposomes of the present invention are used, it is possible to have a larger amount of the iodine compound accumulated in macrophages as compared with a contrast medium utilizing a suspension or an oil emulsion as a known technique.

Examples of tissues in which localization of macrophages is observed, which can be suitably imaged by the method of the present invention, include blood vessel, liver, spleen, air vesicle, lymph node, lymph vessel, and renal epithelium. Further, it is known that macrophages accumulate in lesions in certain classes of diseases. Examples of such diseases include tumor, arteriosclerosis, inflammation, infection and the like. Therefore, lesions of such diseases can be identified by using the liposomes of the present invention. In particular, it is known that foam macrophages, which take up a large amount of denatured LDL with the aid of scavenger receptors, accumulate in atherosclerosis lesions at an early stage (Am. J. Pathol., 103, 181 (1981); Annu. Rev. Biochem., 52, 223 (1983)). Therefore, by performing radiography after accumulation of the liposomes of the present invention in the macrophages, it is possible to identify locations of atherosclerosis lesions at an early stage, which is hardly achievable by other means.

The method for radiography utilizing the liposomes of the present invention is not particularly limited. Radiography can be performed by, for example, irradiating an X-ray in the same manner as that in radiography methods utilizing ordinary contrast media for X-ray radiography. Moreover, it is also possible to perform radiography by a nuclear medicinal method by forming liposomes using the compound of the present invention containing a radioisotope of iodine and using the liposomes as a contrast medium for scintigraphy. A kind of the radioisotope of iodine is not particularly limited. Preferred examples include $^{122}$I, $^{123}$I, $^{125}$I, and $^{131}$I, and particularly preferred examples are $^{123}$I and $^{125}$I. A radioactively labeled compound can be synthesized by a known method described in Appl. Radiat. Isot., 37 (8), 907 (1986) and the like after a corresponding unlabeled compound is synthesized. When the hydrophobic compound is a triiodobenzene derivative, it is preferred that at least one of three iodine atoms on the same benzene ring is replaced with a radioisotope. It is preferred that two or more of the atoms are replaced with radioisotopes, and it is most preferred that three of the atoms are replaced with the same kind of radioisotopes.

EXAMPLES

The present invention will be explained more specifically with reference to the examples. However, the scope of the present invention is not limited to the following examples. The compound numbers used in the examples correspond to the numbers of the compounds mentioned above as preferred compounds. Structures of compounds mentioned in the examples were verified by NMR spectra.

Example 1

Dichloromethane (200 mL) was added with hexadecanedioic acid (10.0 g), 2,4,6-triiodophenol (8.3 g) and N,N-dimethylaminopyridine (0.2 g), further added with ethyldimethylaminopropylcarbodiimide (4.0 g), and stirred at room temperature for one day. After the insoluble solids were removed by filtration, the obtained filtrate was concentrated and purified by silica gel column chromatography to obtain mono(2,4,6-triiodophenyl) hexadecanedioate (3.9 g, yield: 30%). In the same manner as that used for mono(2,4,6-triiodophenyl) hexadecanedioate, mono(2,4,6-triiodophenyl) heptadecanedioate was obtained from heptadecanedioic acid.

Ethanol (70 mL) was added with 12-bromododecanoic acid (4.8 g) and 2,4,6-triiodophenol (9.1 g) and the mixture was refluxed for dissolution. The solution was added with potassium hydroxide (2.2 g) and stirred for 12 hours. The precipitates obtained were separated by filtration, washed with ethanol and added with chloroform and 1 N hydrochloric acid to conduct extraction with chloroform twice. After the organic layer was dried over anhydrous magnesium sulfate, the solvent was removed, and the resulting residue was purified by silica gel column chromatography to obtain 12-(2,4,6-triiodophenoxy)dodecanoic acid (7.0 g, yield: 60%). In the same manner as the synthetic method of 12-(2,4,6-triiodophenoxy)dodecanoic acid, 16-(2,4,6-triiodophenoxy)hexadecanoic acid was synthesized from 16-bromohexadecanoic acid.

Dimethylformamide (DMF, 20 mL) was added with ethyl 7-bromoheptanoate (4.7 g) and 2,4,6-triiodophenol (2.4 g), further added with potassium carbonate (2.1 g) and stirred at room temperature for one day. The reaction solution was added with water and extracted twice with ethyl acetate, and the organic layer was washed three times with water and dried over anhydrous magnesium sulfate. Then, the solvent was removed, and the resulting residue was purified by silica gel column chromatography to obtain ethyl 7-(2,4,6-triiodophenoxy)heptanoate (6.0 g, yield: 96%).

Ethanol (95%, 30 mL) was added with of ethyl 7-(2,4,6-triiodophenoxy)heptanoate (4.0 g) and the mixture was refluxed for dissolution, and the solution was added with sodium hydroxide (0.5 g) and further refluxed for 1.5 hours. The crystals obtained were separated by filtration, washed with ethanol and added with dichloromethane and 1 N hydrochloric acid to conduct extraction twice with dichloromethane. The organic layer was dried over anhydrous magnesium sulfate, and then the solvent was removed. The resulting residue was purified by silica gel column chromatography to obtain 7-(2,4,6-triiodophenoxy)heptanoic acid (3.4 g, yield: 90%).

In the same manner as that used for 7-(2,4,6-triiodophenoxy)heptanoic acid, 11-(2,4,6-triiodophenoxy)undecanoic acid was obtained from methyl 11-bromoundecanoate.

Dichloromethane (20 mL) was added with methyl 9-hydroxynonanoate (2.1 g) and pyridine (1.8 g), stirred at 0° C., added with methanesulfonyl chloride (1.3 mL), gradually warmed to room temperature and stirred for one day. The reaction solution was added with water and then extracted twice with dichloromethane. The resulting organic layer was washed with 1 N hydrochloric acid and saturated sodium hydrogencarbonate solution. The organic layer was dried over anhydrous sodium sulfate, and then the solvent was removed. The resulting residue was purified by silica gel column chromatography to obtain methyl 9-(methanesulfonyloxy)nonanoate (2.1 g, yield: 68%).

In the same manner as that used for 7-(2,4,6-triiodophenoxy)heptanoic acid, 9-(2,4,6-triiodophenoxy)nonanoic acid was obtained by using methyl 9-(methanesulfonyloxy)nonanoate.

Methanol (150 mL) was added with 15-pentadecalactone (25.6 g), further added with 28% sodium methoxide solution (50 mL) and refluxed for 3 hours. The reaction solution was added with 1 N hydrochloric acid and extracted three times with ethyl acetate. The organic layer was washed with saturated brine and dried over anhydrous magnesium sulfate, and the solvent was removed to obtain methyl 15-hydroxypentadecanoate (28.5 g, yield: 98%).

In the same manner as that used for 9-(2,4,6-triiodophenoxy)nonanoic acid, 15-(2,4,6-triiodophenoxy)pentadecanoic acid was obtained by using methyl 15-hydroxypentadecanoate.

According to the method described in Synth. Commun., 17, 1339 (1987), monomethyl tridecanedioate was obtained by using tridecanedioic acid. Further, according to the method described in Aust. J. Chem., 48, 1893, (1995), methyl 13-hydroxytridecanoate was obtained by using monomethyl tridecanedioate.

In the same manner as that used for 9-(2,4,6-triiodophenoxy)nonanoic acid, 13-(2,4,6-triiodophenoxy)tridecanoic acid was obtained by using methyl 13-hydroxytridecanoate.

In the same manner as that used for 13-(2,4,6-triiodophenoxy)tridecanoic acid, 14-(2,4,6-triiodophenoxy)tetradecanoic acid was obtained by using tetradecanedioic acid.

In the same manner as that used for 13-(2,4,6-triiodophenoxy)tridecanoic acid, 20-(2,4,6-triiodophenoxy)eicosanoic acid was obtained by using eicosanedioic acid.

According to the method described in Arch. Pharm. (Weinheim) 328, 271 (1995), addition of two carbon atoms was performed to 15-(2,4,6-triiodophenoxy)pentadecanoic acid by using diethyl malonate to obtain 17-(2,4,6-triiodophenoxy)heptadecanoic acid.

In the same manner as that used for 17-(2,4,6-triiodophenoxy)heptadecanoic acid, 19-(2,4,6-triiodophenoxy)nanodecanoic acid was obtained by using 17-(2,4,6-triiodophenoxy)heptadecanoic acid.

In the same manner as that used for 17-(2,4,6-triiodophenoxy)heptadecanoic acid, 21-(2,4,6-triiodophenoxy)heneicosanoic acid was obtained by using 19-(2,4,6-triiodophenoxy)nanodecanoic acid.

Compounds 1-1-1 to 1-1-12, 1-4-4, 1-4-5, 2-1-1 to 2-1-12, 2-4-4, and 2-4-5 were prepared by the method described in J. Med. Chem., 29 (12), 2457 (1986).

Compound 1-1-1:
¹H-NMR (300 MHz, CDCl₃) δ: 8.04 (4H, s) 4.23-4.05 (5H, m) 3.93 (4H, t, J=6.4 Hz) 2.39 (4H, t, J=6.4 Hz) 1.90 (4H, quin, J=6.4 Hz) 1.70 (4H, quin, J=6.4 Hz) 1.64-1.52 (4H, m) 1.52-1.38 (4H, m)

Compound 1-1-2:
¹H-NMR (300 MHz, CDCl₃) δ: 8.04 (4H, s) 4.23-4.05 (5H, m) 3.93 (4H, t, J=6.4 Hz) 2.35 (4H, t, J=6.4 Hz) 1.90 (4H, quin, J=6.4 Hz) 1.70-1.58 (4H, m) 1.58-1.46 (4H, m) 1.46-1.30 (12H, m)

Compound 1-1-3:
¹H-NMR (300 MHz, CDCl₃) δ: 8.04 (4H, s) 4.23-4.05 (5H, m) 3.93 (4H, t, J=6.4 Hz) 2.35 (4H, t, J=6.4 Hz) 1.90 (4H, quin, J=6.4 Hz) 1.70 -1.58 (4H, quin, J=6.4 Hz) 1.58-1.46 (4H, m) 1.46-1.30 (20H, m)

Compound 1-1-4:
¹H-NMR (300MHz, CDCl₃) δ: 8.04 (4H, s) 4.23-4.05 (5H, m) 3.93 (4H, t, J=6.4 Hz) 2.35 (4H, t, J=6.4 Hz) 1.90 (4H, quin, J=6.4 Hz) 1.70-1.58 (4H, m) 1.58-1.46 (4H, m) 1.46-1.30 (24H, m)

Compound 1-1-5:
¹H-NMR (300 MHz, CDCl₃) δ: 8.04(4H, s) 4.23-4.05 (5H, m) 3.93 (4H, t, J=6.4 Hz) 2.35 (4H, t, J=6.4Hz) 1.90 (4H, quin, J=6.4Hz) 1.70-1.58 (4H, quin, J=6.4 Hz) 1.58-1.46 (4H, m) 1.46-1.30 (28H, m)

Compound 1-1-6:
¹H-NMR(300 MHz, CDCl₃) δ: 8.04 (4H, s) 4.23-4.05 (5H, m) 3.93 (4H, t, J=6.4 Hz) 2.35 (4H, t, J=6.4 Hz) 1.90 (4H, quin, J=6.4 Hz) 1.70-1.58 (4H, m) 1.58-1.46 (4H, m) 1.46-1.30 (32H, m)

Compound 1-1-7:
¹H-NMR(300 MHz, CDCl₃) δ: 8.04 (4H, s) 4.23-4.050 (5H, m) 3.93 (4H, t, J=6.4 Hz) 2.35 (4H, t, J=6.4 Hz) 1.90 (4H, quin, J=6.4 Hz) 1.70-1.58 (4H, quin, J=6.4 Hz) 1.58-1.46 (4H, m) 1.46-1.30 (36H, m)

Compound 1-1-8:
¹H-NMR (300 MHz, CDCl₃) δ: 8.04 (4H, s) 4.23-4.05 (5H, m) 3.93 (4H, t, J=6.4 Hz) 2.35 (4H, t, J=6.4 Hz) 1.90 (4H, quin, J=6.4 Hz) 1.70-1.58 (4H, m) 1.58-1.46 (4H, m) 1.46-1.30 (40H, m)

Compound 1-1-9:
¹H-NMR (300 MHz, CDCl₃) δ: 8.04 (4H, s) 4.23-4.05 (5H, m) 3.93 (4H, t, J=6.4 Hz) 2.35 (4H, t, J=6.4 Hz) 1.90 (4H, quin, J=6.4 Hz) 1.70-1.58 (4H, m) 1.58-1.46 (4H, m) 1.46-1.30 (44H, m)

Compound 1-1-11:
¹H-NMR (300 MHz, CDCl₃) δ: 8.04 (4H, s) 4.23-4.05 (5H, m) 3.93 (4H, t, J=6.4 Hz) 2.35 (4H, t, J=6.4 Hz) 1.90 (4H, quin, J=6.4 Hz) 1.70-1.58 (4H, m) 1.58-1.46 (4H, m) 1.46-1.30 (52H, m)

Compound 1-1-12:
¹H-NMR (300 MHz, CDCl₃) δ: 8.04 (4H, s) 4.23-4.05 (5H, m) 3.93 (4H, t, J=6.4 Hz) 2.35 (4H, t, J=6.4 Hz) 1.90 (4H, quin, J=6.4 Hz) 1.70-1.58 (4H, m) 1.58-1.46 (4H, m) 1.46-1.30 (60H, m)

Compound 1-4-4:
¹H-NMR (300 MHz, CDCl₃) δ: 8.04 (4H, s) 4.23-4.05 (5H, m) 2.66 (4H, t, J=6.4 Hz) 2.35 (4H, t, J=6.4 Hz) 1.82 (4H, quin, J=6.4 Hz) 1.70-1.58 (4H, m) 1.58-1.46 (4H, m) 1.46-1.30 (32H, m)

Compound 1-4-5:
¹H-NMR (300 MHz, CDCl₃) δ: 8.04 (4H, s) 4.23-4.05 (5H, m) 2.66 (4H, t, J=6.4 Hz) 2.35 (4H, t, J=6.4 Hz) 1.82 (4H, quin, J=6.4 Hz) 1.70-1.58 (4H, m) 1.58-1.46 (4H, m) 1.46-1.30 (36H, m)

Compound 2-1-1:
¹H-NMR (300 MHz, CDCl₃) δ: 8.04 (4H, s) 4.78 (5H, m) 3.93(4H, t, J=6.4 Hz) 2.39 (4H, t, J=6.4 Hz) 1.90 (4H, quin, J=6.4 Hz) 1.73 (4H, quin, J=6.4 Hz) 1.64-1.52 (4H, m) 1.52-1.38 (4H, m)

Compound 2-1-2:
¹H-NMR(300 MHz, CDCl₃) δ: 8.04 (4H, s) 4.78 (4H, s) 3.93(4H, t, J=6.4 Hz) 2.42 (4H, t, J=6.4 Hz) 1.90 (4H, quin, J=6.4 Hz) 1.72-1.60 (4H, m) 1.60-1.46 (4H, m) 1.46-1.30 (12H, m)

Compound 2-1-3:
¹H-NMR (300 MHz, CDCl₃) δ: 8.04 (4H, s) 4.78 (4H, s) 3.93 (4H, t, J=6.4 Hz) 2.42 (4H, t, J=6.4 Hz) 1.90 (4H, quin, J=6.4 Hz) 1.72-1.60 (4H, m) 1.60-1.46 (4H, m) 1.46-1.30 (20H, m)

Compound 2-1-4:
¹H-NMR (300 MHz, CDCl₃) δ: 8.04 (4H, s) 4.78 (4H, s) 3.93 (4H, t, J=6.4 Hz) 2.42 (4H, t, J=6.4 Hz) 1.90 (4H, quin, J=6.4 Hz) 1.72-1.60 (4H, m) 1.60-1.46 (4H, m) 1.46-1.30 (24H, m)

Compound 2-1-5:
¹H-NMR (300 MHz, CDCl₃) δ: 8.04 (4H, s) 4.78 (4H, s) 3.93 (4H, t, J=6.4 Hz) 2.42 (4H, t, J=6.4 Hz) 1.90 (4H, quin, J=6.4 Hz) 1.72-1.60 (4H, m) 1.60-1.46 (4H, m) 1.46-1.30 (28H, m)

Compound 2-1-6:
¹H-NMR (300 MHz, CDCl₃) δ: 8.04 (4H, s) 4.78 (4H, s) 3.93 (4H, t, J=6.4 Hz) 2.42 (4H, t, J=6.4 Hz) 1.90 (4H, quin, J=6.4 Hz) 1.72-1.60 (4H, m) 1.60-1.46 (4H, m) 1.46-1.30 (32H, m)

Compound 2-1-7:
¹H-NMR (300 MHz, CDCl₃) δ: 8.04 (4H, s) 4.78(4H, s) 3.93(4H, t, J=6.4 Hz) 2.42 (4H, t, J=6.4 Hz) 1.90 (4H, quin, J=6.4 Hz) 1.72-1.60 (4H, m) 1.60-1.46 (4H, m) 1.46-1.30 (36H, m)

Compound 2-1-8:
¹H-NMR (300 MHz, CDCl₃) δ: 8.04 (4H, s) 4.78(4H, s) 3.93(4H, t, J=6.4 Hz) 2.42 (4H, t, J=6.4 Hz) 1.90 (4H, quin, J=6.4 Hz) 1.72-1.60 (4H, m) 1.60-1.46 (4H, m) 1.46-1.30 (40H, m)

Compound 2-1-9:
¹H-NMR (300 MHz, CDCl₃) δ: 8.04 (4H, s) 4.78(4H, s) 3.93(4H, t, J=6.4 Hz) 2.42 (4H, t, J=6.4 Hz) 1.90 (4H, quin, J=6.4 Hz) 1.72-1.60 (4H, m) 1.60-1.46 (4H, m) 1.46-1.30 (44H, m)

Compound 2-1-11:
¹H-NMR (300 MHz, CDCl₃) δ: 8.04 (4H, s) 4.78(4H, s) 3.93(4H, t, J=6.4 Hz) 2.42 (4H, t, J=6.4 Hz) 1.90 (4H, quin, J=6.4 Hz) 1.72-1.60 (4H, m) 1.60-1.46 (4H, m) 1.46-1.30 (52H, m)

Compound 2-1-12:
¹H-NMR (300 MHz, CDCl₃) δ: 8.04 (4H, s) 4.78(4H, s) 3.93(4H, t, J=6.4 Hz) 2.42 (4H, t, J=6.4 Hz) 1.90 (4H, quin, J=6.4 Hz) 1.72-1.60 (4H, m) 1.60-1.46 (4H, m) 1.46-1.30 (60H, m)

Compound 2-4-4:

$^1$H-NMR (300 MHz, CDCl$_3$) δ: 8.04 (4H, s) 4.78 (4H, s) 2.68 (4H, t, J=6.4 Hz) 2.32 (4H, t, J=6.4 Hz) 1.80 (4H, quin, J=6.4 Hz) 1.72-1.53 (4H, m) 1.53-1.18 (36H, m)

Compound 2-4-5:

$^1$H-NMR (300 MHz, CDCl$_3$) δ: 8.04 (4H, s) 4.78 (4H, s) 2.68 (4H, t, J=6.4 Hz) 2.32 (4H, t, J=6.4 Hz) 1.80 (4H, quin, J=6.4 Hz) 1.72-1.53 (4H, m) 1.53-1.18 (40H, m) 1.46-1.30 (36H, m)

TEST EXAMPLE 1

Uptake Amount of Iodine Atoms by Vascular Smooth Muscle Cells

Dipalmitoyl-PC (Funakoshi, No. 1201-41-0225) and dipalmitoyl-PS (Funakoshi, No. 1201-42-0237) at the ratio shown below were dissolved in chloroform together with each of the iodine compounds of the present invention in an eggplant-shaped flask according to the method described in J. Med. Chem., 25 (12), 1500 (1982) to form a uniform solution. Then, the solvent was evaporated under reduced pressure to form a thin membrane on the bottom of the flask. This thin membrane was dried in vacuum, then added with an appropriate amount of 0.9% physiological saline (Hikari Pharmaceutical, No. 512) and subjected to ultrasonication (No. 3542 probe type oscillator, Branson, 0.1 mW) for 5 minutes under ice cooling to obtain a uniform liposome dispersion. The diameters of the liposomes in the resulting dispersion were measured by using WBC analyzer (A-1042, Nihon Kohden). As a result, the diameters were found to be 40 to 65 nm. The liposome preparations mentioned below, which were produced by the above method, were each added to a mixed culture system of vascular smooth muscle cells and macrophages described in Japanese Patent Application No. 2001-018573. The cells were cultured at 37° C. under 5% CO$_2$ for 24 hours, and the amounts of the iodine compounds taken up into the vascular smooth muscle cells were each quantified. The compounds of the present invention can be efficiently taken up by vascular smooth muscle cells, and it is clearly understood that they have superior properties as component lipid of liposomes for contrast medium for X-ray radiography.

TABLE 1

|  |  | Uptake amount |
| --- | --- | --- |
| PC 50 nmol + PS 50 nmol + 1-1-3 | 150 nmol | 42.8 × 10$^{-3}$ nmol/μg protein |
| PC 50 nmol + PS 50 nmol + 1-1-5 | 150 nmol | 43.7 × 10$^{-3}$ nmol/μg protein |
| PC 50 nmol + PS 50 nmol + 1-1-7 | 150 nmol | 52.1 × 10$^{-3}$ nmol/μg protein |
| PC 50 nmol + PS 50 nmol + 2-1-3 | 75 nmol | 36.3 × 10$^{-3}$ nmol/μg protein |
| PC 50 nmol + PS 50 nmol + 2-1-7 | 75 nmol | 39.6 × 10$^{-3}$ nmol/μg protein |
| PC 50 nmol + PS 50 nmol + 1-13-3 | 150 nmol | 40.1 × 10$^{-3}$ nmol/μg protein |

TEST EXAMPLE 2

X-Ray Radiography of Rat Arteriosclerotic Lesion

Figure 1:
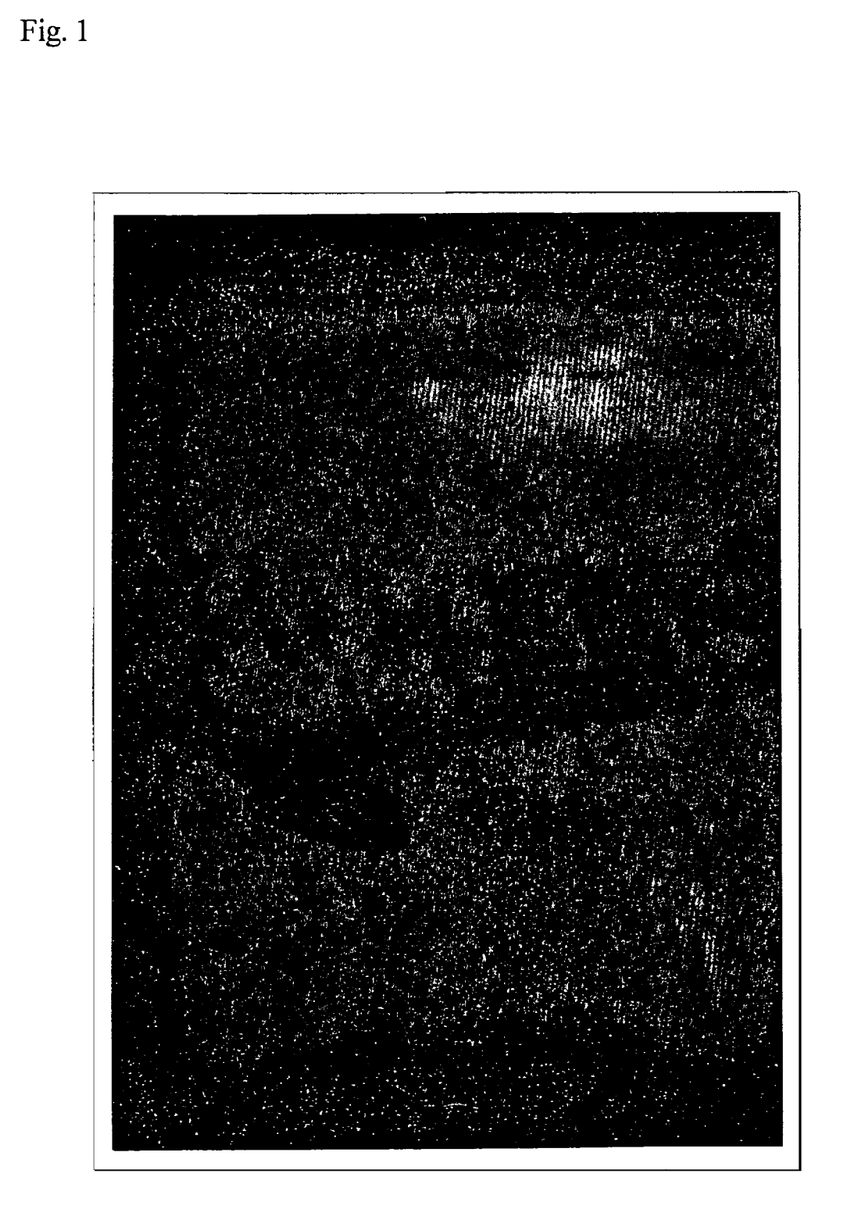
FIG. 1 is a photograph showing the result of X-ray radiography of a rat arteriosclerotic lesion using a liposome preparation containing a compound of the present invention (Compound 1-1-3).
Figure 2:
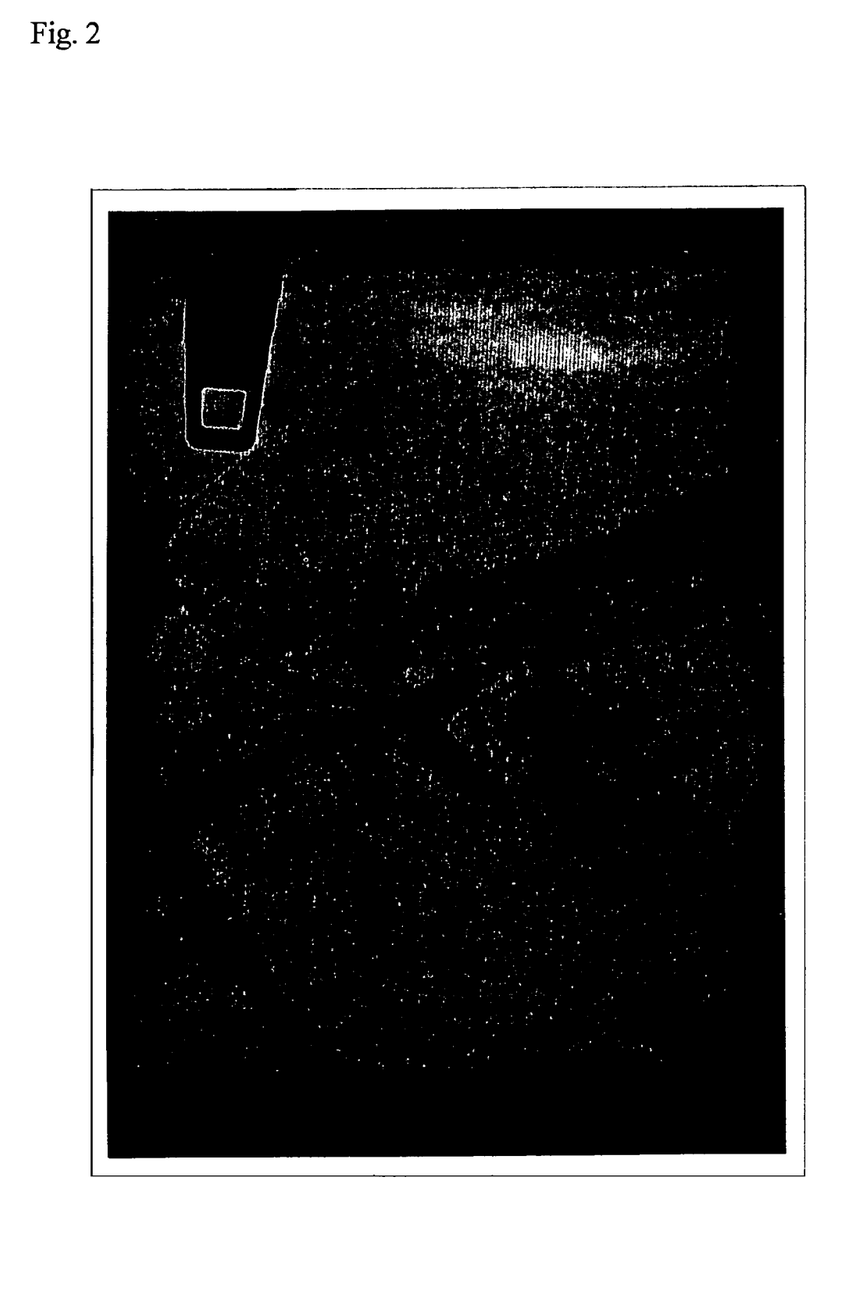
FIG. 2 is a photograph showing the result of X-ray radiography of a rat arteriosclerotic lesion using a liposome preparation containing a compound of the present invention (Compound 1-13-3).

According to the method described in Invest. Radiol., 18, 275 (1985), arteriosclerotic lesions were formed in rat aortas. Each of the liposome preparations of Compounds 1-1-3 and 1-13-1 was carefully administered to the rats with the formed arteriosclerotic lesions from the cervical vein in an amount of 200 mg/kg. Five minutes after the administration, clearly contrasted images of the arteriosclerotic lesions were obtained by X-ray radiography. The results are shown in FIGS. 1 and 2.

TEST EXAMPLE 3

Toxicity Test by Continuous Administration for Three Days in Mice

Six-week old ICR male mice (Charles River Japan) were purchased, and after quarantine for 1 week, acclimatized in a clean animal cage (air-conditioning: HEPA filter of class 1000, room temperature: 20 to 24° C., humidity: 35 to 60%). Then, in order to obtain an MTD value, a liposome preparation was administered from the caudal vein. The liposome preparation was administered by using physiological saline (Hikari Pharmaceutical) or a glucose solution (Otsuka Pharmaceutical) as a solvent. On the basis of the MTD value obtained, the liposome preparation was administered everyday from the caudal vein for three consecutive days in an amount corresponding to ½ of the MTD value (n=3). The symptoms were observed up to 6 hours after each administration, and autopsy was performed after completion of the administration to examine major organs. As a result, no abnormality was recognized.

TABLE 2

| Compound: MTD (mg/kg) | | | | | |
| --- | --- | --- | --- | --- | --- |
| 1-1-1: | 800 mg/kg | 1-1-3: | 800 mg/kg | 1-1-4: | 1000 mg/kg |
| 1-1-5: | 800 mg/kg | 1-1-7: | 800 mg/kg | 1-1-8: | 800 mg/kg |
| 1-1-9: | 1000 mg/kg | 1-12-3: | 800 mg/kg | 1-13-3: | 1000 mg/kg |
| 2-1-1: | 800 mg/kg | 2-1-4: | 1000 mg/kg | 2-1-8: | 1000 mg/kg |

TEST EXAMPLE 4

Preparation of S9 and Degradation Test

Six-week old male SD rats (Charles River Japan) were purchased and acclimatized for 1 week. After the acclimatization for 1 week, the rats were weighed and bled by decapitation. The liver was extracted and washed three times with chilled 0.15 M KCl. After the washing, wet weight of the liver was determined, and the liver was added with the three-times weight of chilled 0.15 M KCl and placed in a homogenizer. The liver was homogenized under ice cooling, and the homogenate was centrifuged with cooling at 9000 g for 10 minutes. The supernatant obtained was designated S9 and stored below −80° C.

The stored S9 was thawed in running water. The thawed S9 (0.1 ml) was added with 0.4 M MgCl$_2$ (0.02 ml), 1.65 M KCl (0.02 ml) and 0.2 M Na phosphate buffer (pH 7.4, 0.5 ml), added with glucose-6-phosphate (Oriental Yeast), NADPH (Oriental Yeast) and NADH (Oriental Yeast) so as to give a concentration of 4 μM, and added with distilled water to give a total volume of 1 ml (this solution is referred to as "S9 Mix"). S9 Mix (0.1 ml) was added with a test substance so as to give a concentration of 5 μg/ml and shaken at 37° C. under reciprocal movement. The weight of the test substance (unchanged substance) with passage of time in the S9 Mix was measured by HPLC. The test substance was dissolved in dimethyl sulfoxide (Wako Pure Chemical Industry) beforehand. The results are shown as percentage values of the amount of the unchanged substance after 30 minutes based on the amount of the unchanged substance immediately after the addition to S9 Mix, which is taken as 100%. It is clearly understood that the compounds of the present invention were efficiently degraded in the S9 degradation test, and that they have superior properties as lipid components of liposomes for a contrast medium for X-ray radiography.

TABLE 3

| 1-1-1: | 10% | 1-1-2: | 0% | 1-1-4: | 10% |
|---|---|---|---|---|---|
| 1-1-5: | 0% | 1-1-6: | 0% | 1-1-9: | 0% |
| 1-1-11: | 0% | 1-4-4: | 20% | 1-4-5: | 10% |
| 1-12-3: | 10% | 1-13-3: | 0% | 2-1-1: | 0% |
| 2-1-2: | 20% | 2-1-4: | 10% | 2-1-8: | 20% |
| 2-1-9: | 0% | 2-12-3: | 0% | 2-13-3: | 0% |

INDUSTRIAL APPLICABILITY

The compounds of the present invention have superior properties as membrane components of liposomes for a contrast medium for X-ray radiography and contrast medium for scintigraphy, and a lesion of vascular disease and the like can be selectively contrasted by X-ray radiography using the liposomes containing these compounds.

What is claimed is:

1. A compound represented by the following general formula (I) or a salt thereof:

wherein $Ar^1$ and $Ar^2$ independently represent a substituted or unsubstituted aryl group having at least one iodine atom as a substituent; $L^1$ and $L^2$ independently represent a divalent bridging group having a main chain with a carbon number of 7-30 and containg at least one heteroatom; and X represents —CH(OH)— or —CO—.

2. The compound or a salt thereof according to claim 1, wherein X is —CH(OH)—.

3. The compound or a salt thereof according to claim 1, wherein $Ar^1$ and $Ar^2$ independently represent a phenyl group having at least three iodine atoms as substituents.

4. A liposome containing the compound or a salt thereof according to claim 1 as a membrane component.

5. The liposome according to claim 4, which contains a combination of a phosphatidylcholine and a phosphatidylserine as membrane components.

6. A contrast medium for X-ray radiography, which comprises the liposome according to claim 4.

7. The contrast medium for X-ray radiography according to claim 6, which is used for radiography of a vascular disease.

8. The contrast medium for X-ray radiography according to claim 6, which is used for radiography of vascular smooth muscle cells which are abnormally proliferated under an influence of foam macrophages.

9. The contrast medium for X-ray radiography according to claim 6, which is used for radiography of a tissue or a lesion where macrophages localize.

10. The contrast medium for X-ray radiography according to claim 9, wherein the tissue where macrophages localize is selected from the group consisting of tissues of liver, spleen, air vesicle, lymph node, lymph vessel, and renal epithelium.

11. The contrast medium for X-ray radiography according to claim 9, wherein the lesion where macrophages localize is selected from the group consisting of lesions of tumor, inflammation, and infection.

12. A liposome containing the compound or a salt thereof according to claim 1 as a membrane component, wherein at least one of the iodine atoms is a radioisotope.

13. A contrast medium for scintigraphy, which comprises the liposome according to claim 12.

14. The contrast medium for scintigraphy according to claim 13, which is used for scintigraphy of vascular smooth muscle cells which are abnormally proliferated under an influence of foam macrophages.

15. The contrast medium for scintigraphy according to claim 13, which is used for scintigraphy of a tissue or lesion where macrophages localize.

16. The contrast medium for scintigraphy according to claim 13, wherein an objective tissue of scintigraphy is selected from the group consisting of tissues of blood vessel, liver, spleen, air vesicle, lymph node, lymph vessel, and renal epithelium.

17. The contrast medium for scintigraphy according to claim 13, which is used for scintigraphy of a lesion selected from the group consisting of lesions of tumor, arteriosclerosis, inflammation, and infection.

* * * * *